US009131953B2

(12) United States Patent
Baur et al.

(10) Patent No.: US 9,131,953 B2
(45) Date of Patent: Sep. 15, 2015

(54) SURGICAL INSTRUMENT WITH DIGITAL DATA INTERFACE

(75) Inventors: Thomas Baur, Rottenburg-Hailfingen (DE); Marc Kegreiss, Tuebingen (DE); Peter Selig, Hechingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 706 days.

(21) Appl. No.: 13/400,995

(22) Filed: Feb. 21, 2012

(65) Prior Publication Data

US 2012/0232540 A1  Sep. 13, 2012

(30) Foreign Application Priority Data

Mar. 10, 2011 (EP) .................................... 11157710

(51) Int. Cl.
| | |
|---|---|
| *A61B 17/3203* | (2006.01) |
| *A61B 18/02* | (2006.01) |
| *A61B 17/00* | (2006.01) |
| A61B 18/14 | (2006.01) |
| A61B 18/00 | (2006.01) |

(52) U.S. Cl.
CPC ............. *A61B 17/3203* (2013.01); *A61B 17/00* (2013.01); *A61B 18/02* (2013.01); *A61B 18/14* (2013.01); *A61B 2017/00199* (2013.01); *A61B 2018/00916* (2013.01)

(58) Field of Classification Search
CPC ............... A61B 17/320069; A61B 17/320092; A61B 2017/2904; A61B 2017/2929; A61B 18/085; A61B 17/320068
USPC .......................................................... 606/34
See application file for complete search history.

(56) References Cited

U.S. PATENT DOCUMENTS

| | | | | |
|---|---|---|---|---|
| 6,071,281 A * | 6/2000 | Burnside et al. | ................. | 606/41 |
| 6,074,388 A * | 6/2000 | Tockweiler et al. | ............ | 606/34 |
| 6,142,994 A * | 11/2000 | Swanson et al. | ................. | 606/41 |
| 6,228,079 B1 * | 5/2001 | Koenig | ........................... | 606/34 |
| 6,471,659 B2 * | 10/2002 | Eggers et al. | ................. | 600/564 |
| 7,479,140 B2 | 1/2009 | Ellman et al. | | |
| 7,503,917 B2 | 3/2009 | Sartor et al. | | |
| 7,696,877 B2 * | 4/2010 | Barnes et al. | .............. | 340/572.1 |

(Continued)

FOREIGN PATENT DOCUMENTS

| | | | |
|---|---|---|---|
| CN | 101765414 A | 6/2010 | |
| CN | 101896131 A | 11/2010 | |

(Continued)

*Primary Examiner* — Niketa Patel
(74) *Attorney, Agent, or Firm* — Dickstein Shapiro LLP

(57) ABSTRACT

A surgical instrument that comprises at least one microcontroller arranged in the handle of the instrument and that communicates with the surgical apparatus—without the interposition of a radio link via the cable that already exists between the surgical apparatus and the surgical instrument. Safe data transmission is ensured not only in the high-interference environment of an active RF surgical apparatus, but also in, for example, water jet, argon plasma and cryosurgical apparatuses, endoscopes. A differential transmission technique is selected, wherein one or more conductor pairs (insulated conductors) are utilized, one of the conductors of said conductor pairs transmitting the signal and the other transmitting the inverted signal. By subtracting the two signals, the actual data signal is yielded on the receiver side. If feedback interferences from the environment act on the data transmission link, the subtractions performed on the respective receivers cancels out the interferences.

13 Claims, 1 Drawing Sheet

(56) References Cited

U.S. PATENT DOCUMENTS

| | | | |
|---|---|---|---|
| 2002/0019596 A1* | 2/2002 | Eggers et al. .................. 600/564 |
| 2002/0151889 A1* | 10/2002 | Swanson et al. ................ 606/41 |
| 2003/0069571 A1 | 4/2003 | Treat et al. |
| 2003/0225401 A1* | 12/2003 | Eggers et al. .................. 606/39 |
| 2004/0015079 A1* | 1/2004 | Berger et al. .................. 600/437 |
| 2005/0033285 A1* | 2/2005 | Swanson et al. ................ 606/41 |
| 2005/0267455 A1* | 12/2005 | Eggers et al. .................. 606/32 |
| 2006/0025759 A1 | 2/2006 | Ellman et al. |
| 2006/0041257 A1 | 2/2006 | Sartor et al. |
| 2007/0085496 A1* | 4/2007 | Philipp et al. .................. 318/139 |
| 2008/0077158 A1 | 3/2008 | Haider et al. |
| 2008/0281254 A1* | 11/2008 | Humayun et al. .............. 604/22 |
| 2008/0281301 A1 | 11/2008 | DeBoer et al. |
| 2009/0024161 A1* | 1/2009 | Bonutti et al. ................ 606/213 |
| 2010/0061181 A1* | 3/2010 | Malackowski et al. ....... 366/142 |
| 2010/0152726 A1* | 6/2010 | Cadouri et al. ................ 606/35 |
| 2010/0261961 A1* | 10/2010 | Scott et al. .................... 600/111 |
| 2011/0082486 A1* | 4/2011 | Messerly et al. .............. 606/169 |
| 2011/0121735 A1* | 5/2011 | Penny ..................... 315/111.21 |
| 2011/0125149 A1* | 5/2011 | El-Galley et al. .............. 606/34 |
| 2011/0144729 A1* | 6/2011 | Weber ............................ 607/99 |
| 2011/0276113 A1* | 11/2011 | Cybulski ...................... 607/101 |
| 2012/0041436 A1* | 2/2012 | Ullrich et al. .................. 606/39 |
| 2012/0143182 A1* | 6/2012 | Ullrich et al. .................. 606/45 |
| 2012/0203219 A1* | 8/2012 | Evans et al. .................... 606/33 |
| 2012/0226273 A1* | 9/2012 | Nguyen et al. ................. 606/41 |
| 2012/0232540 A1* | 9/2012 | Baur et al. ..................... 606/10 |
| 2013/0103024 A1* | 4/2013 | Monson et al. ................ 606/33 |
| 2013/0190599 A1* | 7/2013 | Wyeth et al. .................. 600/409 |
| 2013/0197506 A1* | 8/2013 | Evans et al. .................... 606/33 |
| 2013/0345562 A1* | 12/2013 | Barthe et al. .................. 600/439 |
| 2014/0018613 A1* | 1/2014 | Scott et al. .................... 600/102 |
| 2014/0018795 A1* | 1/2014 | Shilev et al. ................... 606/41 |
| 2014/0188101 A1* | 7/2014 | Bales et al. ..................... 606/33 |

FOREIGN PATENT DOCUMENTS

| | | |
|---|---|---|
| DE | 10 2005 044 918 A1 | 2/2007 |
| JP | H05-49647 A | 3/1993 |
| JP | 2006-68537 A | 3/2006 |
| WO | WO 2008/098085 A2 | 8/2008 |
| WO | WO 2008/131357 A1 | 10/2008 |
| WO | WO 2009/074329 A2 | 6/2009 |

* cited by examiner

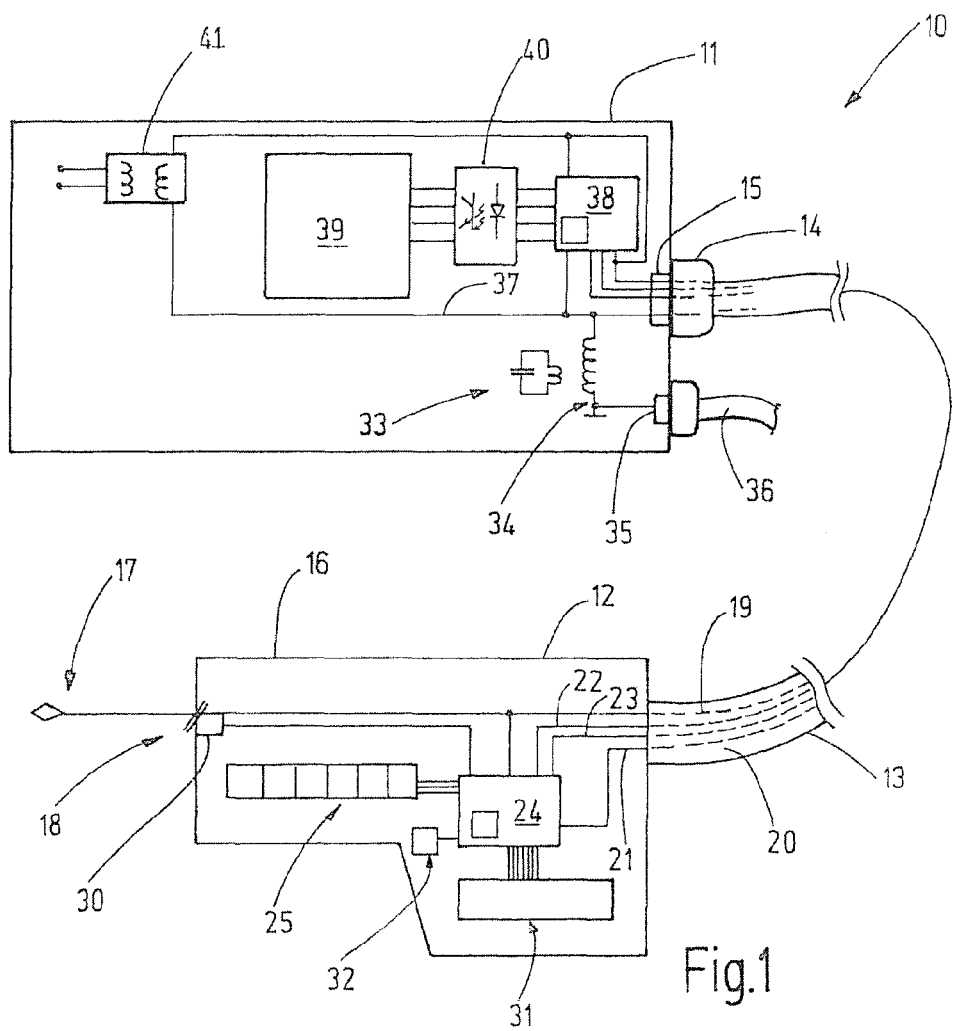
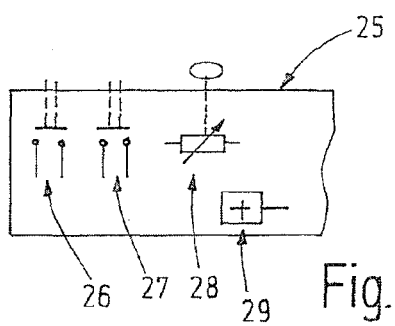
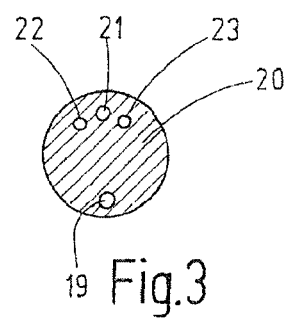
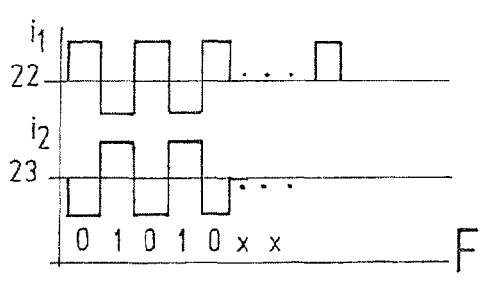
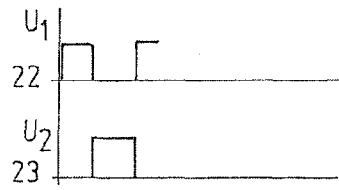

SURGICAL INSTRUMENT WITH DIGITAL DATA INTERFACE

RELATED APPLICATIONS

This application claims priority to European patent application EP 11 157 710.2, filed on Mar. 10, 2011, which is hereby incorporated by reference in its entirety.

TECHNICAL FIELD

The embodiments of the invention relate to a surgical instrument, as well as to a system comprising the surgical instrument and a supplying surgical apparatus.

BACKGROUND

A variety of instruments are used in surgery, said instruments being operated within a surgical system and, in doing so, being powered by a surgical apparatus. Such surgical instruments are, for example, RF surgical instruments provided with electrodes or applicators used for conveying media, said media being different from electric current, to biological tissue at an active site of the operating field. Such active media can be e.g., water, cryomedia or the like. A cable/conduit for the electric current or the other active medium is used between the supplying surgical apparatus and the respectively used instrument.

Frequently, different instruments and accessory parts are provided on a surgical apparatus and driven by said apparatus for operation. The instruments may be of different types. For example, so-called monopolar handles that may be configured as an electric scalpel, a coagulation instrument, a resection instrument or the like, are used. For this, exchangeable electrodes are also frequently used. Bipolar instruments such as e.g., clamps, gripping forceps and the like are also used for coagulating, severing blood vessels or for similar purposes. As a rule, these different instruments require individually specific operating modes for electric activation.

The goal is to ensure that the instrument is not operated in an unsuitable mode. To this end, international publication WO 2009/074329 A2 suggests that the instrument be associated with an RFID transponder that communicates with an instrument antenna. Inside the surgical apparatus, there is an emitter/receiver unit that communicates with the RFID transponder and, in this manner, identifies the connected instrument. Furthermore, this publication suggests the transmission of commands from switches to the surgical apparatus via the RFID transponder, in which case the switches are arranged on the instrument. The instrument may also comprise sensors outputting signals that are being processed and output to the surgical apparatus via the RFID transponder. In doing so, the RFID transponder is arranged as closely as possible to the apparatus, preferably in the plug of the surgical apparatus that is to be connected, or in the connecting cable itself.

Furthermore, U.S. Pat. No. 7,503,917 B2 discloses an instrument that comprises several control switches. These are connected with the surgical apparatus via signal cables. The control switches short-circuit individual resistors of a cascaded voltage divider and thus emit a characteristic voltage signal to the signal cables; said voltage signal being used by the surgical apparatus to detect the switch actuation assigning it to specific switches.

The electrical environment in the operating room is at times subject to very strong interferences. Radio-frequency voltages and currents in the immediate vicinity of the surgical apparatus, surgical instrument and connecting cable lead to high interference field strengths that can negatively affect the signal transmission.

U.S. Pat. No. 7,479,140 B2 also uses analog signal cables for the transmission of switch commands from the surgical instrument to the apparatus, said cables being used to connect diverse characteristic resistors with the surgical apparatus.

Furthermore, German publication DE 10 2005 044 918 A1 discloses a system for the contactless identification and communication between a surgical apparatus and a connected instrument. Again, a transponder that is arranged in the instrument plug of the surgical instrument is used. The associated apparatus socket comprises a reading unit that communicates with the transponder. Many adjustments of the surgical apparatus need to be made directly on the apparatus; the surgeon has only a few adjustment options on the instrument.

SUMMARY

Considering the above, it is an object of the embodiments of the invention to provide a surgical instrument that allows improved adjustment options. Furthermore, a surgical apparatus interacting with the instrument is also disclosed. Finally, a surgical system that comprises a surgical apparatus and at least one surgical instrument with convenient adjustment options on the instrument is also provided.

The above object is achieved by providing a surgical instrument that comprises at least one microcontroller arranged in the handle of the instrument and that communicates with the surgical apparatus—without the interposition of a radio link—via the cable that already exists between the surgical apparatus and the surgical instrument.

It should be appreciated that other programmable components such as, for example, DSP, FPGA, CPLD, or an ASIC, may be used instead of the microcontroller.

By installing the microcontroller in the handle, it is possible to provide control elements on the handle, said control elements allowing the control of many functions of the surgical apparatus. For example, it is possible to provide switches that can be actuated in a configurable manner depending on the situation. In doing so, each switch may be assigned several functions; in which case, the selection of the function to be activated by the actuation of the switch depends, for example, on the mode of operation, specific situation, actuation of other switches or the like. For example, a surgical instrument may contain an acceleration sensor that detects the spatial position of the surgical instrument (e.g., whether it is held vertically or horizontally) and controls the functions dependent thereon. This way it is possible to select one of several functions of a push key. In addition, the microcontroller can be used for generating an identification signal and for outputting this signal to the surgical apparatus to report to said apparatus which instrument or which instrument type (electrode, etc.) is connected to the surgical apparatus. A corresponding identification device communicating with the microcontroller can be provided e.g., on a change coupling of the handle, where various functional elements such as, for example, electrodes can be connected to said identification device. The microcontroller can identify the connected functional element using the identification device and output appropriate commands, signals or the like to the surgical apparatus so that said surgical apparatus may automatically perform the appropriate adjustments as needed.

Furthermore, the microcontroller may be provided with an indicator device that directly displays/indicates various types of information on the handle. There may be individual control lamps, displays or the like. In addition to or instead of visual indicators, the display device may also comprise sensory or acoustic indicators. These may be, for example, buzzers, piezo sound transducers or vibration generators in order to provide the surgeon with acoustic signals or haptic signals that can be felt on the handle. The indicator device may also be combined with the control device. For example, illuminated keys may be provided that light up, are extinguished, change the color in which they light up, or the like—during or after an actuation or as a function of other events, measured values, and/or conditions.

The conduit leading from the surgical apparatus to the surgical instrument may be a light-conveying or fluid conveying conduit (fluid or gaseous) or the like. In the preferred case, however, the conduit is an electric cable comprising at least one insulated conductor that carries a voltage or a suitable current for achieving a tissue effect. In the preferred case, this is an RF voltage or an RF current of adequate power. Usually, the frequency is between 100 Hz and 5 MHz. The voltage may be several thousand volts.

Preferably, the cable contains at least one additional insulated conductor for supplying a voltage to the microcontroller, as well as—preferably—two more insulated conductors for data transmission. Preferably, the data are transmitted as electric currents over the two cables. Preferably, the currents on the two data-transmitting cables flow in opposite directions. This enables a safe data transmission at a high data transmission rate, even in a high-interference environment (i.e., in the immediate vicinity of the RF current-conducting insulated conductor of the same cable). The cable may be a few meters long, in which case interference immunity is of particular importance. With the use of the disclosed measure, it is possible to achieve a safe data transmission without complex shielding or similar measures.

With the use of two cables, data is transmitted from the microcontroller to the surgical apparatus and vice versa, preferably as a serial data stream. It is possible to transmit data when the electrode of the surgical instrument is not activated as well as when the electrode is activated.

By providing an indicator device on the surgical instrument it is possible to transmit data from the surgical apparatus to the surgical instrument and display information on the instrument that so far has only been displayed on a picture screen or on another indicator device. This provides the surgeon with extremely far-reaching control of the surgical apparatus without having to avert his/her eyes from the operating field and without having third parties perform the adjustment via a request.

An RF surgical instrument in accordance with the disclosed principles can be designed such that it can be used for monopolar and/or bipolar applications or for a combination of the two applications.

BRIEF DESCRIPTION OF THE DRAWINGS

Hereinafter, exemplary embodiments of the invention are explained in greater detail with reference to drawings, in which:

FIG. 1 is a schematic block diagram of a surgical system comprising a surgical apparatus and surgical instrument connected by a cable;

FIG. 2 is a schematic representation of an input device of the surgical instrument shown in FIG. 1;

FIG. 3 is a schematized cross-sectional illustration of the cable for connecting the surgical instrument to the surgical apparatus;

FIG. 4 is a current/signal graph that illustrates the data flow between the surgical instrument and the surgical apparatus; and FIG. 5 is a voltage/signal graph that illustrates the data flow between the surgical instrument and the surgical apparatus.

DETAILED DESCRIPTION

In the following description, the same reference signs are used for components that are the same or that have the same function. FIG. 1 schematically illustrates a surgical system 10 comprising a surgical apparatus 11 and a surgical instrument 12. For better understanding, the invention is explained here with reference to an RF surgical system, where an RF high voltage represents the active medium acting on the surgical instrument. The invention is not restricted thereto. The details explained hereinafter can also be provided on an instruments using a different active medium, in particular pressurized water, cryofluid or the like.

The surgical instrument 12 and the surgical apparatus 11 are connected to each other by a cable 13, said cable 13 having a length such that the surgical apparatus 11 can be set up at some distance from the patient—for example, in the non-sterile region—while the procedure is being performed with the surgical instrument 12 on the patient. The cable 13 is connected to a socket 15 of the surgical apparatus 11 via a plug 14. In this manner, diverse surgical instruments can be connected to the socket 15 in order to perform different operations.

Considering the present exemplary embodiments and explanations, the surgical instrument 12 is configured as a monopolar instrument. This instrument comprises a handle 16 on which a tool in the form of an electrode 17 is held. The electrode 17 may be, e.g., a cutting electrode in the form of a spatula, or a needle, such as, e.g., a coagulation electrode in the form of a sphere or the like. In order to hold the electrode 17 on the handle 16, a coupling 18 may be provided, said coupling 18 being only symbolically indicated in FIG. 1.

Preferably, the conductor or cable 13 extends from the side of the handle 16 located opposite the coupling 18. Said cable 13 contains at least one duct for supplying the energy form intended for the application to the biological tissue from the surgical apparatus 11 to the surgical instrument 12. In the present exemplary embodiment, this conductor duct is configured as an insulated conductor 19 (i.e., as an electrical conductor enclosed by the insulating material 20 shown in FIG. 3). Because the exemplary instrument 12 is being shown/described as an RF surgical instrument, the insulated conductor 19 carries an RF high voltage at least part of the time. In conjunction with this, "high voltage" is understood to be any voltage above a protective extra-low voltage of 42 V. In many cases, the peak value of this high voltage is in the range of several thousand volts.

The cable 13 contains additional insulated conductors 21, 22, 23 that are configured as electrical conductors embedded in the insulating material 20.

A microcontroller 24 is arranged in the handle 12. This microcontroller may contain a memory or may communicate with a separate memory (EPROM). Preferably, the ground connection of the microcontroller 24 is connected to the insulated conductor 19, two of its input and output ports are connected to the insulated conductors 22, 23, and its mains voltage connection is connected to the insulated conductor 21 that conducts the electric energy required for operating the microcontroller.

Preferably, the microcontroller 24 is permanently in operation as soon as the instrument 12 is connected to the surgical apparatus 11 and the surgical apparatus 11 is switched on. The microcontroller 24 may be provided with a program that outputs an identification signal to the surgical apparatus 11—either once when the apparatus is switched on or, alternatively, also from time to time—to identify itself; in doing so, the signal provides the surgical apparatus 11 with information regarding the type of connected instrument. The identification signal is emitted as an identification code. The identification code can be analyzed in the surgical apparatus 11 to perform a preliminary setting and/or preliminary selection of appropriate operating modes, effects, etc. that match the instrument 12.

Control elements 25 can be provided on the handle 16, said elements potentially comprising one or more push keys, one or more rotary knobs, one or more position sensors, one or more acceleration sensors or the like, or any combination thereof. Push keys, rotary knobs or the like may be illuminated or combined with other indicating mechanisms that are connected to the microcontroller 24. In addition to the control elements 25, it is possible to provide sensor elements that detect certain measured values, e.g., temperatures, and output these as a signal to the microcontroller. The microcontroller is capable of processing the measured values and/or of reporting them to the surgical apparatus 11.

FIG. 2 schematically shows the control elements 25. Only as an example, two push keys 26, 27, a potentiometer 28 and a position sensor 29 are shown; said position sensor being able to differentiate between e.g., horizontal and vertical positioning of the handle 16. Preferably, the control elements 25 are only connected with the microcontroller 24. Consequently, there is no direct cable connection between the control elements 25 and the surgical apparatus 11.

An identification device 30 may be provided on the coupling 18, said identification device being used to detect the type and/or size of the tool (i.e., an electrode 17 in the described exemplary embodiment) connected to the coupling 18. For example, the identification device 30 may be a socket that is associated with a coding plug of the electrode 17. The identification device 30 may be any suitable technical mechanism that is able to detect a feature encoding the type and/or size of the tool 17. Such a feature may be a part of the dimension of a corresponding element such as e.g., a finger or a projection, as well as an arrangement of several structures such as e.g., recesses or projections.

In addition, the microcontroller 24 can be connected with a display or indicating device 31, said device comprising e.g., an LCD display, an LED display or any other graphical display arrangement, control lamps or the like. The display device 31 can be combined completely or partially with the control elements 25. For example, the display device 31 may comprise touch-sensitive or pressure-sensitive areas so as to allow inputs.

For additional signal output, it is possible to provide acoustic generators and/or a vibration generator 32 that can pass vibrations into the handle 16. A vibration generator 32 may be a motor comprising a small, eccentrically supported weight.

In FIG. 1, the surgical apparatus 11 comprises a generator 33 that is only schematically shown and that is disposed to output RF power and to supply it to the insulated conductor 19 via the socket 15. The generator 33 supplies RF power with reference to the zero potential 34 that is applied to a neutral socket 35. Connected to said neutral socket 35 is a cable 36, the end of which is provided with a not specifically shown neutral electrode for the large-area attachment to the patient. In addition, the neutral socket 35 can be used for the connection of bipolar apparatus.

The cable 37 conducting the RF high voltage being supplied by the generator 33 represents the reference potential for a second microcontroller 38 that is used for communication with the instrument-side microcontroller 24. The microcontroller 38 receives the mains voltage from a separate supply unit 41, e.g., in the form of a power supply, that also feeds the instrument-side microcontroller 24 via the insulated conductor 21. In addition, the socket 15 is used to connect the microcontroller 38 to the two insulated conductors 22, 23 used for data transmission. The microcontroller 38 also communicates with the apparatus control 39 via a potential dividing device 40, e.g., in the form of optocouplers.

The surgical system 10 described so far functions as follows:

If a specific surgical instrument 12 is to be used, said instrument is connected by plugging the plug 14 into the surgical apparatus 11. As a result of this, the microcontroller 24 is provided with the main voltage. It can now perform various actions e.g., emitting an identification code. In doing so, the microcontroller 24 uses the two insulated conductors 22, 23 of the cable 13 for data communication. FIG. 4 shows the levels on the two cables or insulated conductors 22, 23 separately. The transmitting bits are preferably transmitted as current signals or as voltage signals with opposing polarity. For example, a zero bit with positive current i1 is transmitted through the insulated conductor 22 and with negative current i2 through the insulated conductor 23. In order to transmit a logic one (1), both currents reverse their polarity. When the two insulated conductors 22, 23 are not conducting any current, no bit will be transmitted. When only one of the two insulated conductors 22 conducts current, and the other does not, this is interpreted as an interference pulse and, consequently, no valid bit is detected. FIG. 5 illustrates the associate voltages on insulating conductors 22, 23. If the rated voltage on the insulated conductor 22 is equal to one, the rated voltage of zero is applied to the other insulated conductor, and vice versa.

Independent of the electromagnetic irradiation, the data transmission can be made relatively safe already on an electronic/physical level. Safety can be increased even further when the conductors 22, 23 that are insulated relative to each other are twisted together or, optionally, also twisted together with the insulated conductor 21.

An existing readiness status of the instrument 12 can now be signaled e.g., using the display device 31 on the handle 16. In addition, the instrument 12 can receive inputs that are instantly or also later transmitted as a data stream to the surgical apparatus 11. These inputs can be e.g., the selection of various modes, the adjustment of the intensity of the effect, the adjustment of specific operating durations or times or the like. In doing so, the elements 25 may have multiple assignments, whereby the occupancy levels are selected e.g., by selection keys, selection switches or also by positioning the handle 16 e.g., in a vertical or horizontal position. The latter can be detected by the microcontroller 24 via the position sensor 29. When the keys are illuminated, they may change their color depending on the selection of the occupancy level. The selection of the occupancy level can also be indicated or acknowledged in another way.

The push keys 26, 27 can be used e.g., for activating the generator 33 and for thus providing the RF power to the electrode 17. When push key 26 is used and actuated for this purpose, the microcontroller 24 converts this command into a corresponding data stream, said data stream encoding this command. The microcontroller 38 receives this data stream and forwards the command to the apparatus control 39. The apparatus control 39 activates the generator 33, depending on the selected operating mode, with the corresponding voltage parameters, current parameters and output parameters. The microcontroller 24 detects the release of the push key 26 and, consequently, sends a stop command to the microcontroller 38 and, thus, to the apparatus control 39 via the latter microcontroller. Accordingly, the generator 33 is stopped again. Adjustments of the type or extent of the effect can also be performed by appropriate inputs using the control elements 25. Preferably, in doing so, the adjustment options are restricted to adjustments that are reasonably useful in conjunction with the specific instrument. The restriction may be effected by the microcontroller 24 or, following the identification of the instrument 12, also by the surgical apparatus 11.

The adjustments are reported via the microcontroller 24 to the surgical apparatus 11 and, at least optionally, also to the display device 31 for display. In this manner, the surgeon can now perform a plurality of adjustments directly via the surgical instrument 12, said adjustment having otherwise had to be performed on the surgical apparatus 11 itself.

The embodiments of the invention make it possible to directly detect and process the switching status of the actuation elements such as e.g., the control elements 25, or measured values, by sensors in the surgical instrument 12, and then send the data as a digital data stream via a serial bidirectional interface from the surgical instrument 12 to the surgical apparatus 11. Alternatively, it is also possible to send data from the surgical apparatus 11 to the instrument 12 to e.g., write them to a memory element, or to actuate an actuator. In principle, it is possible to provide any number of actuating elements or other control elements 25 without requiring a change of the number of electrical connections between the surgical instrument 12 and the surgical apparatus 11. Interference-sensitive analog signals of sensors or similar sources can be directly analyzed in the surgical instrument 12. Using a preferably bidirectional data communication, it is possible to not only report values from the surgical instrument 12 to the surgical apparatus 11, but it is also possible to activate the functions of the instrument 12 through the surgical apparatus 11. In an electronic memory, the surgical instrument 12 is able to hold data for the identification of the respective instrument by the surgical apparatus 11.

Finally, an electronic assembly of the surgical apparatus 11 communicates—via a wire-bound, bidirectional data transmission link—with an electronic assembly in the surgical instrument 12. Both assemblies comprise, preferably, at least one microcontroller.

Considering the high-interference environment of an active RF surgical apparatus 11, but also considering water jet and cryosurgical apparatuses, a safe data transmission is ensured herein. Preferably, a differential transmission technique is selected, in which case one or several conductor pairs (insulated conductors 22, 23) are used, one of said conductors transmitting the signal and the other transmitting the inverted signal. By subtracting the two signals, the actual data signal is yielded on the receiver side. If there is interference due to feedback from the environment affecting the data transmission link (i.e., the cable), this occurs to the same extent due to the spatial closeness and, optionally, the twisting of the two conductors, these interferences are canceled out due to the subtractions performed on the respective receivers.

It is possible to provide a dedicated conductor pair for each direction of the data transmission or, as previously described, it is possible to provide a single conductor pair 22, 23 for both transmission directions. Consequently, full duplex mode as well as half duplex mode are possible.

It is possible to utilize the RF voltage conductor as the reference potential for data transmission. The reference potential can be conveyed through a suitable dedicated insulated conductor that is connected to the RF conductor on the apparatus side, the instrument side, or also on both sides. Alternatively, it is also possible to select the RF conductor itself as the data signal/ground conductor.

Safe data transmission is ensured not only in the high-interference environment of an active RF surgical apparatus 11, but also in water jet, argon plasma and cryosurgical apparatus, endoscopes or the like. Preferably, a differential transmission technique is selected, in which case one or more conductor pairs (insulated conductors 22, 23) are utilized, one of the conductors of said conductor pairs transmitting the signal and the other transmitting the inverted signal. By subtracting the two signals, the actual data signal is yielded on the receiver side. If feedback interferences from the environment act on the data transmission link (i.e., the cable), this is equally due to the spatial proximity and, optionally, the twisting of the two conductors, these interferences are canceled out as a result of the subtractions performed on the respective receivers.

Details of one or more embodiments are set forth in the accompanying drawings and description. Other features, objects, and advantages will be apparent from the description, drawings, and claims. Although a number of embodiments of the invention have been described, it will be understood that various modifications can be made without departing from the scope of the invention. Also, it should also be understood that the appended drawings are not necessarily to scale, presenting a somewhat simplified representation of various features and basic principles of the invention. The invention is not intended to be limited by any portion of the disclosure and is defined only by the appended claims.

What is claimed is:

1. An RF surgical system comprising:
   a supplying surgical apparatus for supplying an active medium, the supplying surgical apparatus comprising an apparatus microcontroller;
   an RF conductor connected to the apparatus microcontroller as a ground-reference potential;
   a cable for carrying the active medium and connected to the surgical apparatus; and
   an RF surgical instrument connected to the supplying surgical apparatus by the cable, said RF surgical instrument comprising:
      a handle connected to the cable;
      at least one functional element coupled to the handle and configured to be supplied with the active medium by the supplying surgical apparatus;
      a plurality of control elements arranged on the handle; and
      an instrument microcontroller arranged on the handle and connected to the control elements, said instrument microcontroller being supplied with electrical energy via the cable and communicating with the surgical apparatus via the cable by transmitting data via data communications,
   wherein two insulated conductors for data transmission are provided in the cable, and the instrument microcontroller sends and/or receives the data to be transmitted on one insulated conductor and inverted data on the other insulated conductor.

2. The RF surgical system of claim 1, wherein the RF surgical instrument further comprises a display device provided on the handle, said display device being connected to and controlled by the instrument microcontroller.

3. The RF surgical system of claim 2, wherein the display device comprises sensory, visual and/or acoustic indicating means.

4. The RF surgical system of claim 3, wherein the instrument microcontroller is configured to display information received from the surgical apparatus via the cable using the display device.

5. The RF surgical system of claim 1, wherein the active medium is an RF electrical current, and the cable comprises an RF voltage conducting insulated conductor.

6. The RF surgical system of claim 1, wherein the active medium is a fluid or light, and the cable comprises at least one insulated conductor for conveying the active medium.

7. The RF surgical system of claim 1, further comprising at least one insulated conductor provided in the cable for conveying a voltage supply to the instrument micorcontroller.

8. The RF surgical system of claim 1, wherein at least one of said two insulated conductors is connected to the instrument microcontroller.

9. The RF surgical system of claim 1, wherein the data is transmitted as a serial data stream in the cable.

10. The RF surgical system of claim 1, wherein the data is transmitted as current pulses.

11. The RF surgical system of claim 1, wherein the instrument microcontroller is configured to emit an instrument-specific identification code at least once following connection to the surgical apparatus.

12. The RF surgical system of claim 1, wherein the instrument microcontroller is configured to convert signals of the control elements into commands for the surgical apparatus.

13. The RF surgical system of claim 1, wherein the instrument microcontroller is associated with the apparatus microcontroller, said apparatus microcontroller being electrically connected, via the cable, to the instrument microcontroller accommodated in the handle.

* * * * *